United States Patent [19]

Buttery et al.

[11] Patent Number: 5,405,618
[45] Date of Patent: Apr. 11, 1995

[54] BIOMOSAIC POLYMER OBTAINED BY EMULSION POLYMERIZATION OF HYDROPHOBIC MONOMERS IN THE PRESENCE OF BIOACTIVE MATERIALS

[75] Inventors: Howard J. Buttery, Newport; Patrick L. Coleman, Minneapolis; Dean S. Milbrath, West Lakeland, all of Minn.

[73] Assignee: Minnesota Mining and Manufacturing Company, St. Paul, Minn.

[21] Appl. No.: 972,082

[22] Filed: Nov. 5, 1992

Related U.S. Application Data

[63] Continuation of Ser. No. 681,418, Apr. 4, 1991, abandoned, which is a continuation of Ser. No. 439,630, Nov. 21, 1989, abandoned.

[51] Int. Cl.$^6$ .......................... A61K 9/00; C08G 2/02; C08J 5/22
[52] U.S. Cl. .................. 424/486; 424/487; 424/94.1; 436/531; 436/534; 436/535; 435/180; 522/71; 522/87; 522/85; 522/72; 526/200; 526/201
[58] Field of Search ............... 424/78, 81, 94.1, 409, 424/486, 487; 526/199, 200, 201; 436/531, 534, 535; 435/180; 522/71, 87, 85, 72

[56] References Cited

U.S. PATENT DOCUMENTS

| | | | |
|---|---|---|---|
| Re. 27,444 | 7/1972 | Will | 260/2.5 R |
| 3,709,805 | 1/1973 | Krauch et al. | 204/159.22 |
| 3,788,950 | 1/1974 | Hicks et al. | 195/103.5 R |
| 3,793,445 | 2/1974 | Updike et al. | 424/12 |
| 3,859,169 | 1/1975 | O'Driscoll et al. | 195/63 |
| 4,021,364 | 5/1977 | Spieser et al. | 252/316 |
| 4,036,808 | 7/1977 | Pembaum et al. | 260/42.51 |
| 4,321,117 | 3/1982 | Kaetsu et al. | 204/159.16 |
| 4,322,311 | 3/1982 | Lim et al. | 252/316 |
| 4,379,038 | 4/1983 | Kaetsu et al. | 204/159.12 |
| 4,452,892 | 6/1984 | Rosevear | 435/180 |
| 4,466,931 | 8/1984 | Tanny | 264/22 |
| 4,521,317 | 6/1985 | Candau et al. | 252/8.55 |
| 4,552,633 | 11/1985 | Kumakura et al. | 204/159.21 |
| 4,713,975 | 12/1987 | Tomalia et al. | 73/38 |
| 4,774,178 | 9/1988 | Egerer et al. | 435/180 |
| 5,021,236 | 6/1991 | Gries et al. | 424/9 |

FOREIGN PATENT DOCUMENTS

| | | | |
|---|---|---|---|
| 0178791 | 4/1986 | European Pat. Off. | |
| 0226470 | 6/1987 | European Pat. Off. | |
| 0292325 | 5/1988 | European Pat. Off. | B01D 13/04 |
| 0294186 | 6/1988 | European Pat. Off. | G01N 33/543 |
| 57-31436 | 7/1982 | Japan | C12N 11/04 |
| 57-42314 | 9/1982 | Japan | C12N 11/04 |
| 1411386 | 10/1975 | United Kingdom | |
| 2071669 | 9/1981 | United Kingdom | |

OTHER PUBLICATIONS

Ericsson et al., Biochim. Biophys. Acta., 1983, 729, pp. 23–27.
Ericsson et al., Biochim Biophys. Acta., 1983, 729, pp. 23–27, A Cubic Protein–Monolein–Water Phase.
Andrade, J., "Surface and Interfacial Aspects of Biomedical Polymers, vol. II Protein Adsorption", Chapter 1, J. Andrade Ed., Plenum Press, N.Y. (1985).
Buchholz et al., Meth. Enzymol. 135, 3–3 (1987).
Galas et al., Radiochem. Radioanal. Let. 43(6), 355–362 (1980).

(List continued on next page.)

*Primary Examiner*—Thurman K. Page
*Assistant Examiner*—Peter F. Kulkosky
*Attorney, Agent, or Firm*—Gary L. Griswold; Walter N. Kirn; John H. Hornickel

[57] ABSTRACT

A biomosaic polymer is provided. Biologically active materials are bound at surfaces of such polymers polymerized from emulsions containing hydrophobic polymerizable monomers, such biologically active materials, and surface active agents. The biomosaic polymers may be formed into membranes, films, beads, or other structures for a variety of assays, bioseparations, or catalyzed reactions and other uses. A single step polymerization of the emulsion provides significant retention of the biologically active material bound and congregated at surfaces of the polymer.

22 Claims, 2 Drawing Sheets

OTHER PUBLICATIONS

Hoffman, A., Radiat. Phys. Chem. 18(1,2), 323–342 (1981).
Kaetsu et al., Radiat. Phys. Chem. 14, 595–602 (1979).
Kaetsu et al., Biotech. Bioeng. 21, 863–873 (1979).
Luisi, P. L., Ange. Chem. Intl. Ed. 24(6), 439–450 (1985).
O'Driscoll et al., Biotech. Bioeng. 14, 847–850 (1972).
Schriven, L. E., Nature 263, 123 (1976).
Stoffer et al., J. Dis. Sci. Tech. 1(4), 393–412 (1980).
Yoshida et al., J. Macromol. Sci.-Chem. A14(4), 555–569 (1980).
Piskin, A. K., NATO ASI Ser C 226, 17–23 (1988).
Carenza et al., Rad. Phys. Chem. 31 (4–6), 657≅662 (1988).
Kawashima et al., Biotech. Bioenginer., 16, 609–621 (1974).
Kaetsu et al., Biotech. Bioenginer., 21, 847–861 (1979).
Nilsson et al., Biochim. Biophys. Acta, 268, 253–256 (1972).
Fukui et al., Methods in Enzymology, vol. 135, 230–252 (1987).
Anderson et al., "Polymer Association Structure Microemulsions and Liquid Crystals", ACS Symposium Series 384, 204–234 (1989).
Sandwick et al., Journal of Colloid and Interface Science, vol. 115, No. 1, 130–138 (1987).
Boccu et al., Applied Biochemistry and Biotechnology, vol. 15, 1–10 (1987).
Proposal 86–05354 to the National Science Foundation and Dec. 10, 1985 cover letter there to.

BIOMOSAIC POLYMER OBTAINED BY EMULSION POLYMERIZATION OF HYDROPHOBIC MONOMERS IN THE PRESENCE OF BIOACTIVE MATERIALS

This is a continuation of application Ser. No. 07/681,418, filed Apr. 4,1991, now abandoned, which is a continuation of application Ser. No. 07/439,630, filed Nov. 21, 1989, now abandoned.

FIELD OF THE INVENTION

The present invention relates to biomosaic polymers having biologically active material bound at surfaces thereof and the method for preparing the same. The polymer may be a porous membrane, and the biologically active material may be useful for biospecific reactions such as immunoassays, bioseparations, enzyme-catalyzed reactions and the like.

BACKGROUND OF THE INVENTION

Special problems are presented in the biochemical reactions used to assay a specific composition in a mixture of materials, separate one material from another, or catalyze a reaction using an enzyme. Frequently, the chemicals or molecules useful for such assays, separations, or reactions are scarce and costly. If such biologically active materials are not attached to a support material by some means, the scarce and costly materials will be lost for further usage, repeat experiments, and the like.

Therefore, in the biochemistry arts, methods involving a sequence of processing steps have been developed to immobilize various biologically active materials to supports where the supports have been formed in the absence of biologically active materials. Generally, such methods of immobilization may be divided into the following categories: covalent bonding or crosslinking of the biologically active material to a support; adsorption onto a support; or inclusion in a polymer matrix wherein the biologically active material is trapped or encapsulated in the lattice of the polymer. (A. Hoffman, Radiat. Phys Chem. 18(1,2), 323-342 (1981)).

However, depending upon the application, immobilization by covalent bonding or crosslinking may damage the biologically active material to the extent that its activity is reduced or lost. (K. Buchholz et al., Meth. Enzymol. 135, 3-30 (1987)). Even if the biologically active material retains its biological activity, experience has shown in production of covalently bonded immobilized materials that the distribution of biologically active materials may not be uniform.

Adsorption of such materials to a surface often results in the loss of activity. Further, adsorption is often a reversible process such that the biologically active material can be lost from the support by equilibration with the reaction media which may cause undesired contamination of the reaction products. (J. Andrade in "Surface and Interfacial Aspects of Biomedical Polymers, Volume II Protein Adsorption", Chapter 1, J. Andrade Ed., Plenum Press, New York (1985)).

Inclusion of the biologically active material by entrapment or encapsulation has previously been a preferred method for enzymes since the method relies upon the physical trapping of a large molecule in a polymer matrix from which it is very slow to escape. (A. Hoffman, referenced above). For materials which interact with the entrapped molecule and which are small enough to diffuse through this matrix, these methods are satisfactory, but for large reaction materials such as large proteins, the matrix prevents enzyme reactions.

Further, entrapment methods conventionally employ gel matrices formed by the polymerization of hydrophilic monomers and crosslinkers to form hydrogels. (U.S. Pat. No. 3,788,950 and K. O'Driscoll et al., Biotech. Bioeng. 14, 849–850 (1972)). These hydrogels are typically mechanically weak and may not be able to withstand the rigors of repeated usage without breaking up. Thus, the biologically active material and its matrix may be lost during the assay, separation, or reaction.

Encapsulations have been performed using gamma irradiation to polymerize hydrophilic monomers in order to trap enzymes, but such radiation polymerization has required the freezing of the enzyme/monomer mixture to encapsulate the enzymes therein. (I. Kaetsu et al., Radiat. Phys. Chem. 14, 595–602 (1979)). Thus, the immobilization of an enzyme in a hydrophilic matrix by this process requires excessive energy. Further, using gamma radiation of high dosages could destroy the biological activity of the enzyme. (E. Galas et al., Radiochem. Radioanal. Let. 43(6), 355–362 (1980)).

Hydrophobic monomers have also been used to entrap enzymes by polymerization of frozen mixtures or dispersions. These processes result in the preparation of beads as the hydrophobic monomers separate into droplets as the water freezes. (I. Kaetsu et al., Biotech. Bioeng. 21, 863–873 (1979)).

Unfortunately, the prior methods of encapsulation or entrapment of biologically active materials do not allow the immobilized species to bind or react with large molecules while retaining the species within the matrix. Encapsulation or entrapment would not allow for the immobilized species to interact with both large and small molecules.

In other words, most of the methods for direct incorporation of biologically active materials into the support relate to supports such as beads, gels, and particles.

Immobilization of biologically active materials onto the surfaces of membrane supports is known, but the active materials are introduced after membrane formation. (European Patent Office, Publication 0 294 186). This can lead to problems of leakage of the biologically active material, or non-uniform distribution of the biologically active material on the support, or require additional processing steps. Membrane supports are particularly desirable for bioseparations, enzyme-catalyzed reactions and the like.

Conventional processes have also been developed for the preparation of emulsions in the presence of biologically active materials. Such emulsions may be either water in oil (W/O) or oil in water (O/W) or other combinations of hydrophilic/hydrophobic liquids. (U.S. Pat. No. 4,774,178).

With the use of some surfactants, biologically active materials may be dispersed into an emulsion which qualifies as a microemulsion because of the microscopic extent of dispersion of the oil and water constituents. (P. L. Luisi, Angew. Chem. Int. Ed. Engl. 24(6), 439–528 (1985)). When the oil and water components of the microemulsion are so dispersed that it is not possible to characterize the microemulsion as either a water in oil microemulsion or an oil in water microemulsion, a bicontinuous microemulsion is recognized. (L. E. Scriven, Nature 263, 123 (1976)).

Thus, the water and oil components of the microemulsion are so intermixed that both components are intimately mixed in continuous contact with like material. A suitable analogy for a bicontinuous microemulsion is a water saturated sponge. Both the water and the sponge components are intimately mixed but each is also in continuous contact with its like material.

Previously processes have used microemulsions to prepare polymers and beads. (J. O. Stoffer et al., J. Dispersion Sci. and Technol. 1(4), 393–412 (1980) and U.S. Pat. No. 4,521,317). However, the polymerization of microemulsions containing biologically active materials has only been used to prepare nanometer-sized particles. (U.S. Pat. No. 4,021,364). Films and membranes, most desired for biological reactions such as assays, separations and enzyme-catalysis, have not been produced by microemulsion techniques.

Thus, what is needed is a polymer formed having biologically active or reactive sites at its surfaces in order to enable biochemical usage. What is also needed is a method of preparing the polymer using a low cost emulsion method which does not harm the bioreactivity of the biologically active material.

SUMMARY OF THE INVENTION

The present invention overcomes the problems in the art by providing a biomosaic polymer having amounts of biologically active material bound at surfaces thereof as to enable biochemical usage. The biomosaic polymer is prepared by polymerizing a liquid/liquid dispersion (i.e., an emulsion) which contains a significant amount of surface active agent to assist in the development of a sufficiently stable emulsion and to assure binding of the biologically active material at the surfaces of the biomosaic polymer.

A "biomosaic polymer" means a polymer having at least one biologically active material bound at surfaces of the polymer formed from a polymerized emulsion of at least one hydrophobic polymerizable monomer polymerized in the presence of such biologically active material. Because biologically active material is present during polymerization, the bioreactive sites are created by such one or more biologically active materials bound at surfaces of the polymer, wherever such surfaces may be located in the structure of the polymer so formed. The biologically active material present in the mass of the biomosaic polymer is congregated at surfaces of such biomosaic polymer where such biologically active material may be biochemically useful.

"Surfaces" means any surface or surfaces of the biomosaic polymer formed, e.g., the outer surfaces of a film or the outer surface and the surfaces of pores of a porous membrane or bead.

"Bound" means that biologically active material is chemically or physically combined with the hydrophobic polymerizable monomer at surfaces formed during polymerization such that at least a minimally useful amount biologically active or reactive sites is exposed.

"Congregated" means that the amount of biologically active material present during polymerization and combining with the hydrophobic polymerizable monomer is overwhelmingly located at surfaces of the biomosaic polymer.

Compared with previously known materials, biologically active material in the biomosaic polymer of the present invention is neither physically entrapped within the polymer interstices nor merely subsequently attached at the surface of a polymer previously prepared.

While not intending to be limited to a particular theory, it is believed that biologically active material present during the polymerization of the polymerizable monomer, as facilitated by the surface active agent, becomes irreversibly part of surfaces of the polymer so formed. With some portion or portions of the molecule(s) of biologically active material contributing to the surface formation of the polymer, that portion or portions of the molecule(s) of biologically active material become(s) bound at surfaces and the remaining portions of the bound molecule(s) of biologically active material not bound. So bound as a part of exposed surfaces of the biomosaic polymer and forming a mosaic of bioreactivity at such surfaces, biologically active material is like cilia prepared to interact with that which passes by.

The unexpectedly large amount of biologically active material bound at surfaces of the biomosaic polymer can be expressed in terms of mass/surface area. It has been found according to the present invention that from as little protein as is minimally useful to as much protein as about 70 $\mu g/cm^2$ of a membrane of such biomosaic polymer can be bound at surfaces of the polymer.

The unexpectedly large amount of biologically active material bound at surfaces of the biomosaic polymer can also be expressed in terms of the efficiency of binding of available protein. It has been found according to the present invention that between about 10 percent and about 50 percent of the protein available was bound at surfaces of the biomosaic polymer. It is believed that between about 1 percent and about 90 percent could be so bound.

The unexpectedly large amount of biologically active material bound at surfaces of the biomosaic polymer can also be expressed in terms of mass/mass comparisons with the biomosaic polymer. Depending on the weight fraction ratio of biologically active material to polymerizable monomer present for polymerization, it has been found according to the present invention that the mass/mass comparison can be between as little as minimally useful to as much as 20 mg/g of biomosaic polymer.

Finally, the unexpectedly large amount of biologically active material bound at surfaces of the biomosaic polymer can also be expressed in terms of a percentage of surface area having biologically active material so bound. It has been found according to the present invention that as little protein as is minimally useful to as much as about 35 percent of the surface area of the biomosaic polymer had biologically active material so bound. It is possible that with as much as 90 percent efficiency of binding as much as about 85 percent of the surface area of the biomosaic polymer could have biologically active material so bound.

It should be understood that the present invention contemplates the binding of one or more kinds of biologically active material with one or more polymerizable monomers and could even exceed the ranges presently known.

At least a three component system is used to prepare the biomosaic polymer having biologically active material bound at the polymer: hydrophobic polymerizable monomer, biologically active material, and surface active agent. These three components are in an emulsion of hydrophobic liquid/hydrophilic liquid. At ambient temperature, the monomer is polymerized in the presence of biologically active material and surface active agent.

In one embodiment of the invention, the emulsion used to prepare the biomosaic polymer can be a two liquid system having multiple components in immiscible liquids: a hydrophobic polymerizable monomer in or as one liquid, and a hydrophilic liquid immiscible with the hydrophobic polymerizable monomer as the other liquid. The biologically active material may be in either liquid or both liquids, although preferably in the hydrophilic liquid prior to mixing to form the emulsion. The surface active agent may be in either liquid or both liquids, although preferably in the hydrophobic liquid prior to mixing to form the emulsion.

The present invention also solves the problems inherent in the use of excessive energy for a polymerization process by conducting such polymerization at ambient temperatures.

The present invention also solves the problems of biochemical reactivity for the assay, bioseparation, catalyzed reaction, or the like, by forming a polymer having a biologically active material bound at surfaces of the biomosaic polymer, thereby permitting facile interaction with both large and small molecules without a loss of that costly and scarce material during each biochemical interaction.

The present invention also provides a polymer, having biologically active material bound at surfaces, formed into various structures, e.g., a film, a porous membrane, a porous bead or particle, a plug, a strand, a string, or a web, among others envisioned by those skilled in the art. Each of these forms may have different utility depending on the type of assay, separation, or reaction employed.

The present invention also solves the problems inherent in subsequent interaction of a biologically active material with a previously formed polymer.

These and other objects of the present invention will become apparent in view of the following description of the invention.

EMBODIMENTS OF THE INVENTION

EMULSION COMPONENTS AND PHASES

The biomosaic polymer having biologically active materials bound at surfaces thereof formed according to the present invention is achieved by the preparation of a hydrophobic liquid/hydrophilic liquid emulsion having three significant components: at least one polymerizable monomer, at least one surface active agent, and at least one biologically active material. Desired forms of emulsions are microemulsions which form spontaneously and have good thermodynamic stability.

Preferably, the hydrophilic liquid is water or any other hydrophilic solvent in which the biologically active material may be stable. Preferably, the hydrophobic liquid is the hydrophobic polymerizable monomer capable of polymerization from a microemulsion.

The amounts of the three components described above used in the emulsion depend on the desired properties of the biomosaic polymer. Proper amounts can be derived from phase diagrams involving all three components or their solvents. Phase diagrams and the various structures which may be adopted by the components prior to polymerization have been described in numerous publications including "Microemulsions: Theory and Practice", ed L. M. Prince, Academic Press, N.Y., 1977, pp. 133–148, and in "Micellization, Solubilization and Microemulsions", Volumes I and II, ed Mittal, K. L., Plenum, New York, 1977, pp 45–53 and references therein which disclosures are incorporated by reference as if fully rewritten herein. One skilled in the art may be able to use such phase diagrams to determine the proper amounts of the components. The phase diagram will change depending upon the components used.

Non-limiting examples of emulsions include oil in water (O/W) emulsions or microemulsions for beads, water in oil (W/O) microemulsions of low water and surface active agent content for films, and W/O microemulsions of higher water and surface active agent content for porous structures such as membranes.

Figure 1:
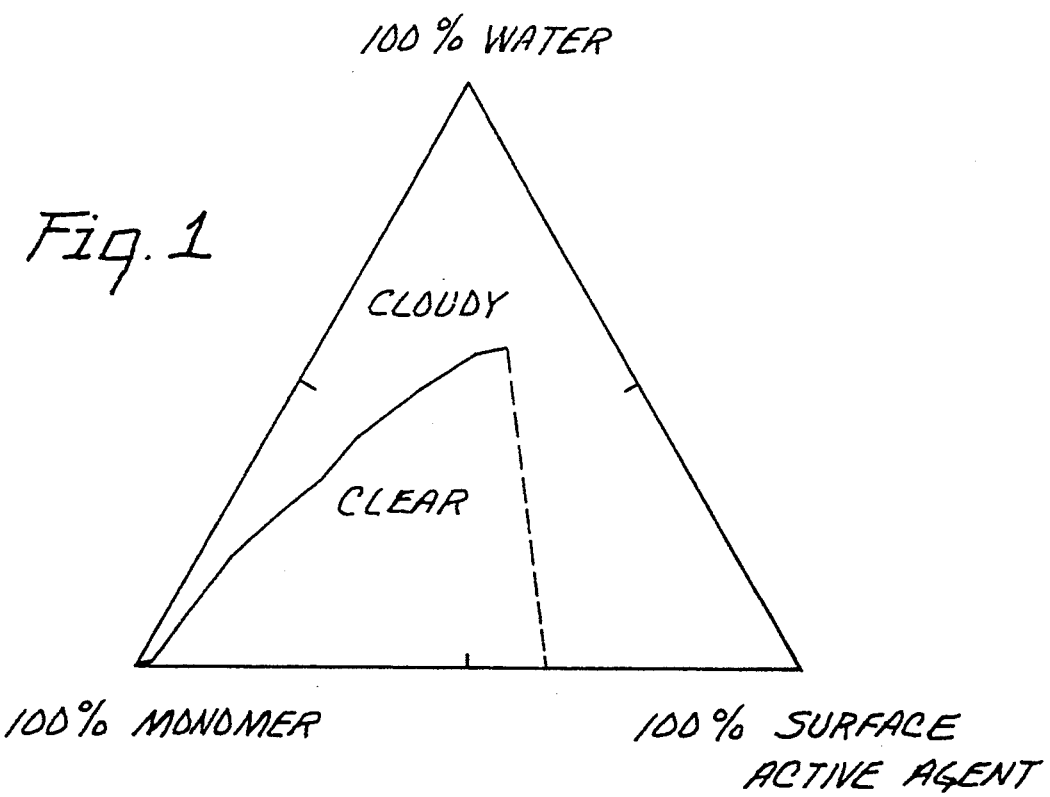
FIG. 1 is a graph showing a phase diagram for one embodiment of the present invention described in Example 1 below.

For the purposes of the present invention to identify the stable clear W/O region, FIG. 1 illustrates a phase diagram comprising at one apex, polymerizable hydrophobic monomer, at the second apex surface active agent, and at the third apex, the hydrophilic liquid, water, into which biologically active material may be placed. Depending on the respective weight fractions of all components, the dispersion ranges from a cloudy emulsion to a clear microemulsion.

While not being bound to any particular theory, in a preferred embodiment of the invention, polymerizable microemulsions comprising polymerizable monomer, surface active agent, and biologically active material in the hydrophilic liquid are believed to have sufficient surface interaction as to provide droplets of hydrophilic liquid containing biologically active material having a diameter in the range of from about 5 nm to about 80 nm and the hydrophobic polymerizable monomer and surface active agent as the continuous medium. As polymerization proceeds, phase separation of the biomosaic polymer occurs during formation. That formation is believed to be facilitated by the intermediate production of bicontinuous or other characteristics as the microemulsion composition changes.

POLYMERIZABLE MONOMER

The polymerizable monomer is present in the "oil" component of the emulsion and is therefore hydrophobic. The polymerizable monomer may be present in the "oil" component in bulk, in dispersion, or in solution. "Hydrophobic" means that the polymerizable monomer has a solubility in water of less than 1 part in 100 parts (weight/weight) of water. However, in the presence of the surface active agent this hydrophobic monomer may become so dispersed as to form a microemulsion in the presence of hydrophilic liquids. By contrast, "hydrophilic" means a water-miscible compound that is capable of forming an emulsion or microemulsion with the "oil" component.

"Monomer" for purposes of this invention means at least one monomer, prepolymer, oligomer, or combinations thereof, capable of forming an emulsion in the presence of a surface active agent and a hydrophilic liquid. The monomer must be polymerizable by methods known in the art, for example, such as described in Volume 4 of "Encyclopedia of Polymer Science and Technology", ed., H. F. Mark et al., Interscience, New York, 1966, pp 331–414, the disclosure of which is incorporated by reference as if fully rewritten herein. Desirably, the polymerizable monomer is polymerizable by irradiation, e.g., using high energy electromagnetic radiation. The oil component may also contain a photoinitiator to facilitate polymerization of the polymerizable monomer.

Generally, hydrophobic polymerizable monomers of the present invention are addition-polymerizable unsaturated organic compounds having at least one double bond between two carbon atoms. Desirably, at least one of these carbon atoms also has bonded thereto a carboxyl or carboxylate ester functionality. Such hydrophobic polymerizable monomers are well known in the radiation-induced polymer coating art, and lists of suitable monomers can be found in publications by J. J. Wildi ("Surface Coatings, Australia", June 1986, p.19); R. Holman ("U.V. and E.B. Curing Formulations for Printing Inks, Coatings and Paints", SITA Technology, London, 1984, pp. 49–60); and U.S. Pat. No. 4,466,931, the disclosures of which are incorporated by reference as if fully rewritten herein.

Of the compositions described above, desirably hydrophobic polymerizable monomers terminated by one or more acrylate groups are useful in the preparation of the polymer in accordance with the present invention. Non-limiting examples include monofunctional acrylates and methacrylates, such as isooctyl acrylate (IOA), isobornyl acrylate (IBA), 2-ethylhexyl acrylate (2-EHA), ethylenediglycol acrylate (EDGA), and ethyltriglycol methacrylate (ETGMA); difunctional acrylates and methacrylates, such as 1,6-hexanediol diacrylate (HDDA), tetraethyleneglycol diacrylate (TEGDA), tripropyleneglycol diacrylate (TPGDA), and propoxylated glycol diacrylate (POGDA); trifunctional acrylates and methacrylates, such as pentaerythritol triacrylate (PETA), and trimethylolpropane triacrylate (TMPTA); and tetrafunctional acrylates and methacrylates, such as pentaerythritol tetraacrylate (PETTA), and di-trimethylolpropane tetraacrylate (DTMPTTA).

Preferably, for the preparation of a flexible, non-fragile polymer structure, a hydrophobic polymerizable monomer having a monofunctional acrylate group, such as isobornyl acrylate (IBA), may be used in combination with one or more polymerizable monomers having multifunctional acrylate groups, such as propoxylated glycol diacrylate (POGDA), in a range of weight percentages of from about 5 percent to about 95 percent of the total weight of all of the hydrophobic polymerizable monomers.

For a preferred practice of the present invention, it is preferable to include a photoinitiator in the hydrophobic polymerizable monomer. A photoinitiator is a molecule which can absorb radiant energy and undergo a chemical process which results in reactive intermediates such as free radicals capable of initiating the polymerization of the hydrophobic polymerizable monomer. Many photoinitiators are known in the art and have been described in part in the publications by Wildi and Holman referenced above. Non-limiting examples include benzoin and its derivatives, benzil ketals, acetophenone derivatives, benzophenones such as Michler's ketone, and anthraquinones. Preferred amounts of the photoinitiator in the hydrophobic polymerizable monomers range from about 0.1 to about 10 weight percent of the hydrophobic polymerizable monomer.

The hydrophobic polymerizable monomers of the present invention are present in an amount of from about 1 percent to about 97 percent of the weight of the emulsion. Desirably, the hydrophobic polymerizable monomers are in an amount of from about 25 percent to about 80 percent of the total weight of the emulsion to obtain porous polymer structures. Preferably, when forming a porous membrane, the amount of the hydrophobic polymerizable monomer in the emulsion is from about 35 percent to about 65 percent of the weight of the emulsion, in order to assure polymer integrity.

SURFACE ACTIVE AGENT

"Surface active agent" means a material which may be nonionic, ionic, or zwitterionic. Ionic includes both cationic and anionic. Generally, the interaction of a protein with a surface is prevented by the presence of a surface active agent. (See, e.g., C. Tanford in the "Hydrophobic Effect", Chapters 12, 16, and 19, J. Wiley and Sons, First Edition (1973)). Unexpectedly, such surface active agents used in accordance with the present invention actually appear to enhance the ability of a polymerizable monomer at the time of polymerization to bind unexpectedly large amounts of the biologically active material at surfaces of the polymer formed. The biologically active material is bound at surfaces of the polymer in such amounts only in the presence of the surface active agent at the time of polymerization.

Surface active agents useful in accordance with the present invention are molecules which consist of a hydrophobic group and a hydrophilic group. One or more surface active agents may be used in accordance with present invention. Many examples and types are known such as described by M. J. Rosen in "Surfactants and Interfacial Phenomena" (Wiley-Interscience, New York, 1978) at pp. 1–25, the disclosure of which is incorporated by reference as if fully rewritten herein. Commercially available surface active agents are listed in "McCutcheon's Detergents and Emulsifiers" (McCutcheon Division, MC Publishing Co., Glen Rock, N.J., published annually through at least 1989), the disclosures of which are incorporated by reference as if fully rewritten herein.

Non-limiting useful examples of anionic surface active agents include salts of carboxylic acids preferably having a carbon chain length of from about 8 to about 22 atoms, sulfonic acids, sulfuric acid esters, and phosphoric and polyphosphoric acid esters.

Non-limiting examples of cationic surface active agents include quaternary ammonium salts, and other salts of amines, diamines, polyamines, amine oxides, or polyoxyethylenated amines; (all such amines preferably having a carbon chain length from about 8 to about 22 atoms).

Non-limiting examples of nonionic surface active agents include polyoxyethylenated-alkyl phenols, polyoxyethylenated-straight chain alcohols, polyoxyethylenated-polyoxypropylene glycols, and carboxylic acid esters preferably having a carbon chain length from about 8 to about 22 atoms.

Non-limiting examples of zwitterionic surface active agents include beta-N-alkylaminopropionic acids, N-alkyl-beta-iminodipropionic acids, imidazoline carboxylates, N-alkylbetaines, sulfobetaines, and sultaines.

Preferred surface active agents are the nonionic surface active agents, in order to minimize degradation of bioactivity of the biologically active material. The actual choice of the surface active agent will depend upon the selection of the other components for the emulsion.

The amount of the surface active agent present in the emulsion will depend upon the solubility of the surface active agent in the hydrophobic polymerizable monomer constituting the "oil" component of the emulsion.

Generally, for the formation of films and membranes, the weight of surface active agent in the emulsion will range from about 2 percent to about 60 percent, in order to assure binding of biologically active material at the surfaces of the polymer. Desirably, in order to assure the formation of a porous polymer such as a membrane, the weight of surface active agent in the emulsion is from about 10 percent to about 50 percent. Preferably, to yield a desirable porous polymer having biologically active material bound at surfaces of the polymer, the weight of the surface active agent in the emulsion is from about 20 percent to about 50 percent.

For the formation of beads, a liquid/liquid dispersion is used. The first liquid is a W/O emulsion described above for the formation of films or membranes. The second liquid is a liquid immiscible with the emulsion, such as water, having a highly water soluble surface active agent dissolved therein. The (W/O)/W emulsion may have surface active agent in a weight percent to the weight of the total complex emulsion of as much as 97 percent. With the surface active agents in both liquids interacting, the polymerizable monomer in the complex emulsion polymerizes into the form of porous beads having the biologically active material bound at surfaces thereof.

BIOLOGICALLY ACTIVE MATERIAL

"Biologically active material" means a substance which is biochemically, immunochemically, physiologically, or pharmaceutically active or reactive. Biologically active material includes at least one or more of the following: biochemical compounds (such as amino acids, carbohydrates, lipids, nucleic acids, proteins, and other biochemicals and substances which may complex or interact with biochemical compounds), such as biochemical compounds biologically functioning as antibodies, antigenic substances, enzymes, co-factors, inhibitors, lectins, hormones, receptors, coagulation factors, growth enhancers, histones, vitamins, drugs, cell surface markers, herbicides, and pesticides, among others known to those skilled in the art. Of the group of biologically active materials described, proteins are frequently desired by those skilled in the art as materials to be immobilized.

Any one or more of the possible biologically active materials may be useful in accordance with the present invention. Non-limiting examples include an allergy diagnosis assay using a membrane having an extract of perennial ryegrass pollen an affinity separation reaction using Protein A for separation of immunoglobulin, or an enzyme-catalyzed reaction using esterase for ester hydrolysis.

Biologically active material can be introduced into the emulsion at any time before polymerization. Preferably, the biologically active material is included in the hydrophilic component prior to formation of the emulsion. The hydrophilic component is preferably water. The amount of biologically active material bound at surfaces of the polymer prepared by the emulsion depends on the concentration of biologically active material in the hydrophilic component.

The concentration of biologically active material in the hydrophilic component can be as little as is minimally useful and up to saturation level. Desirably, biologically active material is present in the hydrophilic component to about 10 weight percent of the total weight of the hydrophilic component to minimize precipitation when included in the microemulsion. Preferably, up to 5 weight percent of biologically active material can be used in the hydrophilic component, both to produce a sufficiently stable emulsion for emulsion processing and to provide subsequently useful bioactivity levels.

The amount of hydrophilic component containing biologically active material in the emulsion can range from about 1 percent to about 97 percent by weight of the emulsion. Desirably, to produce porous structures from microemulsions, the amount can range from about 5 percent to about 50 percent by weight. Preferably, to ensure good physical handling of the components in the emulsion, the amount can range from about 10 percent to about 40 percent by weight.

PREPARATION OF THE POLYMER

The polymerizable emulsions or microemulsions of the present invention are preferably prepared by dispersing or dissolving biologically active material in a hydrophilic solution and, in a separate vessel, mixing the polymerizable monomer and the surface active agent together. The biologically active material in the aqueous solution and the mixture of the surface active agent and the polymerizable monomer are then combined and vigorously mixed together as necessary to give the emulsion or the microemulsion.

Microemulsions are well known to be easily formed with minimal agitation and to be thermodynamically stable. They can be prepared by simply shaking the components together in a stoppered flask for about 10 to 30 seconds at ambient temperatures and pressures. Continuous agitation may be necessary for the less stable emulsions.

The thoroughly mixed emulsion or microemulsion is dispensed, e.g., by extrusion, prilling, spraying, or the like into a receiving vessel which may be but need not serve as a mold for the structure the polymer will take upon polymerization. The dispensed emulsion is then polymerized by any of the known methods referenced above. Desirably, the dispensed emulsion can be polymerized by irradiation with high energy radiation such as ionizing particle radiation (e.g., electron beam emissions) or ionizing electromagnetic irradiation (e.g., gamma irradiation.) Preferably, the radiation is near ultra-violet, ultra-violet, or visible light, and most preferably is ultra-violet light.

Polymerization of the polymerizable monomer in the emulsion or microemulsion in the presence of the surface active agent in order to form a biomosaic polymer having biologically active material bound at surfaces thereof depends on the components used and their weight fractions in the mixture. Desirably, the polymerization conditions are chosen to minimize temperature rises, which could alter the biological activity of the biologically active material. Yet such conditions must allow substantially complete polymerization of the polymerizable monomer as to form the desired biomosaic polymer. For example, the polymerization may use one or more irradiations.

The temperature of the polymerization process may be ambient. There is generally no need for elevated or depressed temperatures for the polymerization process of the present invention. Ambient temperature means the room temperature conditions of laboratories or production facilities throughout temperate climates in the world and therefore ranges of from about 10° C. to about 35° C.

After polymerization is substantially complete, a biomosaic polymer structure is formed having the biologically active material bound at surfaces of the structure, including its outer surfaces and any porous infrastructure surfaces. This structure can be washed, e.g., with solvents such as methanol and water to remove extraneous and unreacted materials.

The resulting washed polymer can be air dried and yields in its preferred form a white, flexible, porous biomosaic polymer suitable for use, e.g., reaction, separation, or assay. Optionally, coloring agents may be added to the emulsion to produce a tinted biomosaic polymer.

USEFULNESS OF THE INVENTION

The presence of surface active agent and biologically active material in the emulsion or microemulsion at the time of polymerization of the polymerizable monomer allows the biologically active material to be bound at the same time as polymerization of the polymerizable monomer. Unlike entrapment or encapsulation techniques used previously, the biologically active material is believed to be a part of the polymer at its surfaces having at least a minimally useful amount of biologically active or reactive sites exposed. Unlike adsorption, covalent bonding or crosslinking, the biologically active material is bound at the time of the polymerization, not at some time subsequently when the processing techniques may be more costly, more damaging to the bioreactivity of the material, or yield fewer or non-uniformly spaced bioreactive sites on the surface of the previously formed substrate.

Use of the emulsion polymerization process at ambient temperatures and pressures, preferably using radiation polymerization techniques, avoids costly emulsion polymerization techniques at freezing temperatures and yields a greater amount of biologically active material at the surfaces of the biomosaic polymer.

Biomosaic polymers formed according to the methods of the present invention retain significant amounts of biologically active material at their surfaces.

Tests are known to measure activity of biologically active material, for example as reported by P. K. Smith et al. in "Measurement of Protein Using Bicinchoninic Acid" *Analytical Biochemistry* 150, 76–85 (1985), which is incorporated by reference as if fully written herein.

In accordance with the present invention, of the constituents and reaction parameters described above, it is possible for one skilled in the art to prepare a biomosaic polymer to retain a biological activity of from about 1 percent to about 90 percent of the original amount of biologically active material in the emulsion, thus demonstrating the significant amount of biologically active material bound at surfaces of the biomosaic polymer. Likely, one skilled in the art can attain an efficiency of binding of biologically active material from about 5 percent to about 75 percent of the amount of biologically active material available in the emulsion. Most likely, one skilled in the art can attain an efficiency of from about 10 percent to about 50 percent.

The biomosaic polymer may be polymerized in the form of an impervious film, a porous membrane, a bead, or extruded into a strand, a string, a web, or molded into any desired three dimensional shape. In each case, the surfaces of the structure are significantly reticular and have biologically active material bound thereat. It is possible to form films, membranes, plugs, strands, strings, and webs, for example, by extruding through a die or by coating on a permanent or temporary support, and immediately passing through an irradiation beam.

Desirably, the biomosaic polymer is in the form of a porous membrane with biologically active material bound at surfaces including the outer surfaces, pores throughout the depth of the membrane and pores into part of the depth of the membrane. Desirably, the pores of the membrane are any suitable size and configuration, e.g., from about 0.01 micrometers to about 10 micrometers. Such porous structures significantly increase the surface area of the biomosaic polymer in order to facilitate uses such as assays, bioseparations, or catalyzed reactions.

When in the form of a membrane, it is within the scope of the present invention to prepare multiple layers of membranes of biomosaic polymers having various biologically active materials bound at surfaces thereof thereby providing multiple functionalities or multiple selectivities for assays, bioseparations, catalyzed reactions, and the like. Further, it is within the scope of the present invention to provide a mixture of beads, some formed by the polymerization of a microemulsion containing one type of biologically active material and the polymerization of a second microemulsion containing another type of biologically active material. Thus, multiple reactivities and selectivities can be provided.

Other structures within the scope of the present invention include multi-functional webs, strands and the like. Also, it is within the scope of the invention to form the biomosaic polymers in multiple polymerization operations to produce concentrically enveloping beads or other layered forms with different biologically active materials in each layer for controlled bioreactivity in sequential usefulness. It is also within the scope of the present invention to produce biologically active powders or particles, e.g., by an additional step of mechanical comminution of bioactive polymer structures prepared from microemulsions in which the monomer and surface active agent components are chosen to impart brittleness to the cured polymer sufficient to yield desired particle size on comminution.

The biomosaic polymers of the present invention are thereby available for a wide range of utility, including enzyme immunoassays, fluorescent immunoassays, chemiluminescent immunoassays, radio immunoassays, catalyzed reactions such as the removal of one of a chiral pair from a reaction mixture, the enzymic conversions, e.g., conversion of starch to glucose using amylase; and affinity separations such as removal of products and/or contaminants from mass culture fermentation/tissue culture reactions or from blood of patients with diseases such as cancer or autoimmune diseases.

It is also within the scope of this invention to have more than one type of biomosaic polymer having the same or different biologically active materials bound at its surfaces. It is also within the scope of the present invention to provide a combination of biomosaic polymers utilizing the same or different surface active agents. By utilizing the variety of reactivities of the principal components in the emulsion, a combination of bioreactivities of the resulting biomosaic polymer with biologically active material bound at its surfaces may be achieved.

It is also within the scope of the present invention to provide a non-reactive support for the biomosaic polymer. For example, non-woven material may be used as the surface on which the emulsion is spread prior to polymerization. Thus, a non-woven material, such as a polyolefin web, or a film serves as the matrix upon which the polymer is secured.

While not intended to be limited, thereto or thereby, the following examples represent the practice and utility of the present invention for a variety of purposes of biological activity.

EXAMPLE 1

This example illustrates the determination of the desired microemulsion region of the phase diagram for one combination of polymerizable monomer acting as the "oil" component, surface active agent, and water useful to include biologically active material therein.

Into 9.5 g of a liquid hydrophobic polymerizable monomer (comprising 85 parts isobornyl acrylate (available from Rohm and Haas of Philadelphia, Pa. as product "QM589"), 10 parts propoxylated glycol diacrylate (Product "Photomer 4083" available from Henkel Corporation, formerly Diamond Shamrock Chemical Corporation, of Morristown, N.J.) and 5 parts of 1-hydroxycyclohexylphenylketone ("Irgacure 184" available from Ciba-Geigy of Hawthorne, N.J.)), was stirred 0.5 g of the surface active agent, dioctyl sodium sulfosuccinate ("Aerosol OT" available from Fisher Scientific of Fairlawn, N.J.). Then water was added drop by drop until the clear solution turned cloudy, indicating the end of the microemulsion region and the onset of a macroemulsion region. This procedure was repeated for a range of monomer:surface active agent ratios up to about 65 weight percent surface active agent at which point the mixture became too viscous to stir. The weight fractions of the components were calculated and plotted to give the delineation of the clear microemulsion region shown in FIG. 1.

EXAMPLE 2

This example illustrates the preparation of a porous biomosaic polymer membrane with bovine serum albumin bound at surfaces of the membrane from a mixture of acrylate monomers and aqueous protein solution. To 4.5 g of a stirred solution of 49 parts by weight of ethyltriglycolmethacrylate ("BM707", Rohm Tech Inc. of Malden, Mass.), 49 parts propoxylated pentaerythritoltriacrylate ("Photomer 4171", Henkel Corporation) and 2 parts 1-hydroxycyclohexylphenylketone ("Irgacure 184", Ciba-Geigy) at 25° C. was added 3.0 grams of dioctyl sodium sulfosuccinate ("Aerosol OT", Fisher Chemical Co.). 1.2 g of this mixture was added to a 1 dram glass vial and mixed with 0.3 g of 5% bovine serum albumin, (BSA) (Sigma Chemical Co. of St. Louis, Mo.) in phosphate buffered saline (PBS), pH 7.0, by shaking for about 10 seconds. (All percent values are weight-percents unless otherwise noted.) The slightly cloudy emulsion which results was poured onto about a 15×15 cm square sheet of polyester film and a second sheet of film was placed on top to spread the emulsion into a thin layer. This assembly was then polymerized by repeated passage through a UV processor (Model "IC120244 AN IRDC", RPC Industries of Plainfield, Ill.) operating at 15.24 meters per minute using two 31 watt/$cm^2$ lamps. To ensure substantially complete polymerization, 20 passes were made on each side. The resulting opaque assembly was washed in 250 ml of methanol for 20 minutes, during which time the polyester sheets were removed. A second methanol wash was followed by 2 washes in 500 ml each of water and air drying to a white, flexible, porous biomosaic polymer membrane.

EXAMPLE 3

This example illustrates the assay method used to determine the total amount of protein bound at surfaces of a biomosaic polymer membrane made by the method of Example 2. A paper punch was used to produce disk samples of the membrane, about 0.7 cm in diameter and 0.2 to 0.7 mm thick, which were then wetted with 50 $\mu$l of water. BCA Protein Assay Reagent (Pierce Chemical Company of Rockford, Ill.), 1 ml, was added and the mixture incubated at room temperature for two hours. After removing the membrane disk, the absorbance of the solution was read at 562 nm. This value was compared to a standard curve prepared concurrently using BSA standards. Samples of a membrane prepared as in Example 2 with water alone instead of BSA solution were also assayed by this method and were found to have no detectable absorbance above background. Additionally samples of membrane were added to the BSA standards and the resulting standard curve was no different from the one prepared without the membrane samples. These experiments indicated that there was no interference from the membrane in the protein determination. Each membrane was sampled in triplicate and the protein values reported as the average and standard deviation of these samples. (Due to the uneven thickness of some membranes the disk samples from a single membrane were not equivalent in mass leading to larger standard deviations than would normally be expected.)

EXAMPLE 4

This example illustrates the method used to determine the amount of protein that was irreversibly bound at surfaces of biomosaic polymer membranes prepared by the method of Example 2. Disk samples of membranes were prepared as in Example 3 and then soaked in 200 microliters of 1% sodium dodecyl sulfate (SDS) in PBS for 1 hour at 37° C. The disks and the SDS solutions were then assayed separately with BCA Protein Reagent as described in Example 3 (50 microliter samples of the SDS solution and 1 milliliter of BCA were used). The amount of protein was calculated by comparison with a standard curve prepared with BSA standards. Each membrane was sampled in triplicate and the results reported as the average and standard deviation of these samples. Using an assay capable of detecting 0.2 $\mu$g of protein, there was no protein detected in the SDS supernate, indicating that the protein was irreversibly bound.

EXAMPLE 5

This example shows that a range of emulsion compositions can be used to bind protein at surfaces of biomosaic polymer membranes. Using the method of Example 2, membranes whose compositions varied in the ratios of protein solution to polymerizable monomer/surface active agent mixture (P/MS), surface active agent to monomer (S/M), and monomer "Photomer 4171" to monomer "BM707" (MD/MB) as indicated in Table 1 (chosen in accord with designed experiment protocol described in Chapter 15 of A. D. Rickmers et al., "Statistics: An Introduction", McGraw-Hill, New York 1967, the disclosure of which is incorporated by reference herein as if fully rewritten), were prepared, washed, and dried. The protein used in preparing these membranes was 1% BSA in water, and the surface active agent used was "Aerosol OT". The concentration of photoinitiator was as in Example 2 in all emulsions. The amount of protein in each resulting membrane was then determined by the analytical methods of Examples 3 and 4 and is summarized in Table 1.

TABLE 1

Membrane Compositions and Amounts of Bound Protein

| Membrane | P/MS | S/M | MD/MB | Protein* (µg/disk) | Post-SDS Protein* (µg/disk) |
|---|---|---|---|---|---|
| 1 | 0.32 | 0.25 | 0.67 | 7.55(0.09) | 3.73(0.79) |
| 2 | 0.32 | 0.25 | 1.0 | 7.07(0.96) | 7.37(0.61) |
| 3 | 0.32 | 0.25 | 1.5 | 4.10(1.10) | 2.19(0.84) |
| 4 | 0.32 | 0.67 | 0.67 | 7.86(1.75) | 5.39(0.31) |
| 5 | 0.32 | 0.67 | 1.0 | 13.62(2.62) | 9.65(0.26) |
| 6 | 0.32 | 0.67 | 1.5 | 10.17(1.62) | 5.48(0.40) |
| 7 | 0.56 | 0.25 | 0.67 | 2.36(0.78) | 1.75(0.27) |
| 8 | 0.56 | 0.25 | 1.0 | 5.68(0.68) | 3.77(0.09) |
| 9 | 0.56 | 0.25 | 1.5 | 4.98(0.92) | 3.68(0.44) |
| 10 | 0.56 | 0.67 | 0.67 | 8.43(0.35) | 7.15(1.27) |
| 11 | 0.56 | 0.67 | 1.0 | 12.05(0.70) | 10.88(0.83) |
| 12 | 0.56 | 0.67 | 1.5 | 10.96(2.32) | 11.89(0.48) |
| 13 | 0.43 | 0.43 | 1.0 | 12.49(1.53) | 9.12(1.76) |
| 14 | 0.14 | 0.67 | 1.0 | 9.18(3.82) | 8.14(4.09) |
| 15 | 0.14 | 1.0 | 1.0 | 5.18(0.64) | 4.23(0.82) |
| 16 | 0.14 | 1.5 | 1.0 | 11.32(1.91) | 8.45(0.50) |
| 17 | 0.22 | 0.67 | 1.0 | 11.86(1.23) | 12.50(1.18) |
| 18 | 0.22 | 1.0 | 1.0 | 12.09(2.59) | 10.27(3.00) |
| 19 | 0.22 | 1.5 | 1.0 | 12.18(1.27) | 10.05(1.59) |
| 20 | 0.32 | 0.67 | 1.0 | 18.82(2.32) | 15.32(1.36) |
| 21 | 0.32 | 1.0 | 1.0 | 17.95(1.50) | 13.55(0.22) |
| 22 | 0.32 | 1.5 | 1.0 | 19.14(1.18) | 15.64(1.86) |

*Standard deviations are shown in parentheses.

Membranes 1, 2, 3, 7, 9, 14, and 16 in Table 1 were found to be more stiff and brittle than the others. This may be due to the low ratio of surface active agent to monomer (membranes 1, 2, 3, 7, and 9) or low protein concentration (membranes 14 and 16) present in the emulsion.

In all formulations protein was found to be bound at surfaces of the biomosaic polymer membrane. On an area basis, this ranged between 8.35 and 67.70 µg/square centimeter of the membrane. The lowest levels occurred at low S/M ratios and the highest at high S/M ratios. It is also readily evident that the levels of protein increase as the amount of protein solution incorporated (P/MS) is increased.

The monomer ratio (MD/MB) has only a slight effect on protein binding, but can change the physical properties and durability of the membrane as indicated above. In these formulations a MD/MB ratio of 1.0 was found to be most acceptable. The amount of protein found to be resistant to SDS treatment was nearly equal to that of the untreated membranes in most cases. (Differences in membrane thickness could account for excess protein in either the treated or untreated membranes.) In no case was protein found in the SDS wash solution of these membranes.

EXAMPLE 6

This example shows that the monomers used to prepare biomosaic polymer membranes can be selected from a wide range of mono-, bi-, tri-, and tetra-functional acrylates. Membranes were prepared from 48 parts of acrylate monomer or 1/1 mixtures by weight of comonomers containing 2% of "Irgacure 184", 36 parts of octylphenoxypolyethoxyethanol ("Triton X-100", Rohm and Haas) and 16 parts of 5% BSA in water by the method of Example 2. The monomers used were methyl methacrylate (MMA; "M5,590–9" Aldrich Chemical Co, of Milwaukee, Wisc.), isobornylacrylate (IBA; "QM589" Rohm and Haas), ethyltriglycolmethacrylate ("BM707"), propoxylated glycoldiacrylate ("Photomer 4083", Henkel Corporation), hexanedioldiacrylate ("Photomer 4017", Henkel Corporation), tripropyleneglycoldiacrylate ("Photomer 4061", Henkel Corporation), aromatic diacrylate ("Photomer 4028", Henkel Corporation), propoxylated pentaerythritoltriacrylate ("Photomer 4171, " Henkel Corporation), trimethylolpropanetriacrylate (TMPTA; "24,680–8" Aldrich Chemical Co.), or di-trimethylolpropane tetraacrylate ("Sartomer-335", Sartomer Chemical Corp. of West Chester, Pa.). After washing and drying the membranes, samples were assayed for protein as in Example 3. The results are shown in Table 2.

TABLE 2

Membrane Compositions and their Bound Protein

| Membrane | Monomer | Comonomer | Protein Found (mg/g of membrane) |
|---|---|---|---|
| 1 | MMA | | DNC* |
| 2 | MMA | Photomer 4083 | 5.78 (0.56) |
| 3 | MMA | Photomer 4171 | 1.83 (0.62) |
| 4 | MMA | Sartomer-335 | 1.95 (1.22) |
| 5 | IBA | | ND** |
| 6 | IBA | Photomer 4083 | ND |
| 7 | IBA | Photomer 4171 | 0.14 (0.08) |
| 8 | IBA | Sartomer-335 | ND |
| 9 | BM707 | | DNC |
| 10 | BM707 | Photomer 4083 | 1.96 (0.28) |
| 11 | BM707 | Photomer 4171 | 5.93 (0.41) |
| 12 | BM707 | Sartomer-335 | 4.89 (0.01) |
| 13 | BM707 | TMPTA | 2.28 (0.51) |
| 14 | BM707 | Photomer 4028 | 7.77 (2.41) |
| 15 | Photomer 4083 | | 6.66 (1.79) |
| 16 | Photomer 4017 | | 2.92 (0.39) |
| 17 | Photomer 4017 | Photomer 4083 | 2.00 (0.70) |
| 18 | Photomer 4017 | Photomer 4171 | 2.15 (0.35) |
| 19 | Photomer 4017 | Sartomer-335 | 1.69 (0.53) |
| 20 | Photomer 4017 | TMPTA | 0.74 (0.07) |
| 21 | Photomer 4017 | Photomer 4028 | 0.42 (0.21) |
| 22 | Photomer 4061 | | 8.13 (0.52) |
| 23 | Photomer 4061 | Photomer 4083 | 2.28 (0.27) |
| 24 | Photomer 4061 | Photomer 4171 | 1.44 (0.33) |
| 25 | Photomer 4061 | Sartomer-335 | 3.61 (0.87) |
| 26 | Photomer 4061 | TMPTA | 1.09 (0.28) |
| 27 | Photomer 4061 | Photomer 4028 | 1.88 (0.52) |
| 28 | Photomer 4028 | | 6.17 (1.46) |
| 29 | Photomer 4028 | Photomer 4083 | 2.89 (0.28) |
| 30 | Photomer 4028 | Photomer 4171 | 3.64 (0.46) |
| 31 | Photomer 4028 | Sartomer-335 | 0.74 (0.23) |
| 32 | Photomer 4171 | | 7.92 (0.82) |
| 33 | TMPTA | | 0.97 (0.21) |
| 34 | Sartomer-335 | | 1.11 (0.29) |

*DNC = The monomer dispersion did not polymerize under these experimental conditions.
**ND = No protein was detected.

All of the monomers used to prepare membranes in this example polymerized to an opaque white membrane. When used without a comonomer MMA and "BM707" did not fully polymerize under these conditions resulting in a gummy oil which could not be evaluated. The handling properties of the product membranes varied as would be expected with increased hardness or brittleness correlating with increased amounts of crosslinking, i.e., the incorporation of greater acrylate functionality. Some protein was detected with at least one formulation of each monomer used, varying from traces to nearly 9 mg of BSA per gram of membrane.

EXAMPLE 7

This example shows that biomosaic polymer membranes can be prepared with nonionic or ionic surface active agents and that the amount of protein bound at surfaces of these membranes is influenced by the type of surface active agents. Membranes were prepared as in Example 2 using 1% BSA solution and an anionic surface active agent, "Aerosol OT" or a nonionic surface active agent, "Triton X-100", (octylphenoxypolyethoxyethanol, Rohm and Haas), "Igepal CO-850" (nonylphenoxypolyethoxyethanol, GAF Corporation of New York, N.Y.), "Pluronic L-81" (polyethoxypolypropoxyethanol, BASF Wyandotte Corporation of Wyandotte, Mich.), or "Pluradot HA410" (Polyoxyalkylene glycol, BASF Wyandotte Corporation). Membranes were also prepared with a cationic surface active agent DDAB (didodecyldimethylammonium bromide, Fisher Chemical Co.) or "Emcol CC9" (Polypropoxy quaternary ammonium chloride, Witco Corporation of New York, N.Y.) from a mixture of 55 parts of a 1/1 monomer mixture of "BM707" and "Photomer 4171" with 2% "Irgacure 184", 35 parts of cationic surface active agent and 10 parts of 5% BSA. The amount of protein was determined by the method of Example 3 and is shown in Table 3.

TABLE 3

Surface Active Agent Used and Amounts of Bound Protein

| Membrane | Agent | Protein Found (mg/g membrane) |
|---|---|---|
| 1 | Aerosol OT | 1.21 |
| 2 | Triton X-100 | 1.47 |
| 3 | Igepal CO-850 | 1.00 |
| 4 | Pluronic L-81 | 2.27 |
| 5 | Pluradot HA410 | 2.37 |
| 6 | DDAB | 1.38 |
| 7 | Emcol CC9 | 4.51 |

These data show that membranes prepared with different types of surface active agents all contain protein and the amount of protein can be changed considerably (over 4-fold) by the choice of surface active agent.

EXAMPLE 8

This example shows that the amount of protein bound at surfaces of a biomosaic polymer membrane depends upon the protein concentration in the hydrophilic liquid of the emulsion. Membranes were prepared as indicated for membrane 5 of Example 5 using 0.0, 0.25, 1.0, and 5.0% of human serum albumin (HSA, Sigma Chemical Co.) in water. As the concentration of protein in the water increased, the dispersion became somewhat cloudy. The membranes were then assayed as in Example 3 and were found to contain 0.0, 0.2, 0.95, and 3.7 mg of HSA per g of membrane, respectively. This indicates that the concentration of protein present in the hydrophilic liquid of the emulsion affects the amount of protein bound at surfaces of the membrane product.

EXAMPLE 9

This example illustrates the preparation of a porous, biomosaic polymer membrane having biologically active material bound at surfaces thereof, supported on a non-reactive support. A slightly cloudy emulsion was prepared by shaking together 9.12 grams of the monomer mixture described in Example 2 and 2.88 grams of a 5% aqueous solution of human serum albumin in a 1 ounce bottle for about 10.0 seconds. A 10 cm by 10 cm piece of non-woven polyester sheet weighing 2 milligrams per square centimeter was then dip coated with the emulsion in a dish and placed between two sheets of polyester film, polymerized with ultraviolet light and washed as in Example 2. The resulting material was a porous membrane supported on an embedded non-woven matrix.

The amount of protein present, assayed by the method of Example 3, was 10.29 mg/gram of membrane. When prepared as a membrane without the non-woven sheet, considerably less human serum albumin, 2.91 mg/gram of membrane, was found to be present. The inclusion of a non-woven sheet not only increased the apparent strength of the product, but also increased the amount of protein.

EXAMPLE 10

This example shows that the ionic strength of the protein in the hydrophilic liquid influences the amount of protein bound at surfaces of the biomosaic polymer membrane. Membranes were prepared as in Example 2 using aqueous solutions of 5% BSA in water, in PBS, or in 2M ammonium sulfate and with "Triton X-100" or "Pluradot HA410". The emulsions which contained PBS were somewhat cloudy while those with ammonium sulfate did not polymerize under these conditions. After washing and drying, the amount of protein found by the method of Example 3 in the water membranes was 1.47 and 2.37 mg/g while the PBS membranes had 1.86 and 4.23 mg/g of membranes, respectively. This indicates that more protein was bound from the PBS solution than the other hydrophilic solutions, and that the ionic strength of the hydrophilic component of the emulsion formulation affects the amount of protein so bound.

EXAMPLE 11

This example shows that much of the available solution protein can be bound at surfaces of the biomosaic polymer membranes. Membranes were prepared as in Example 2 using albumin labeled with radioactive carbon-14 or immunoglobulin G (IgG) labeled with radioactive carbon-14 each diluted with 5% unlabeled BSA. Analysis of the radioactivity present in the product membranes indicated that 34% of the albumin and 47% of the IgG were bound. The radioactive label also showed that in both cases about 1% of the total membrane mass consisted of protein. This indicates that a significant proportion of the available protein can be bound at surfaces of these membranes.

EXAMPLE 12

This example shows that proteins can be bound with or without the use of carrier proteins. Membranes were prepared as in Example 2 using Protein A (available from Genzyme Corporation of Boston, Mass.) or goat antibody to human IgE (available from Immunosearch of Emeryville, Calif.) both labeled with 1-125 using "Iodobeads ™" (available from Pierce Chemical Co.), in 5% BSA or 0% BSA solution. Analysis of the radioactivity remaining in the polymerized, washed and dried membranes showed that 11% of the Protein A and 16% of the antibody were bound when carrier BSA was used. In the absence of carrier BSA the amounts of bound Protein A and antibody increased to 21 and 31%, respectively, despite a large decrease in the total available protein. These data additionally show that the binding of each protein is influenced more by its own properties than that of other proteins present.

EXAMPLE 13

This example shows that DNA can be bound. Membranes were prepared by the method of Example 2 where the aqueous solution contained 0.16 and 0.32 μg of radiolabeled (P-32) DNA and 5% BSA. The DNA preparation was the digestion product of Hae III restriction nuclease on plasmid pBR322. The reaction mixture was then dialyzed to remove low molecular weight fragments, resulting in a solution of 200–600 base pair chains. The membranes produced were determined to contain 24% (38 ng) and 17% (54 ng), respectively, of the DNA initially present in the formulation, by counting the residual radioactivity. These data indicate that DNA can be easily bound.

EXAMPLE 14

This example shows that active enzymes can be bound at surfaces of biomosaic polymer membranes prepared from emulsions containing aqueous solutions of the enzyme. Membranes were prepared with aqueous solutions of 0.025% horseradish peroxidase (HRP) ("Type VI", Sigma Chemical Co.) in 5.0, 2.5, 1.0, 0.25% and 0.0% BSA, PBS as in Example 2. After washing and drying weighed samples of the membranes were assayed for protein content as in Example 3 and for enzyme activity by the method of Doellgast and Rothberger, *Analytical Biochemistry* 147, 529 (1985) (reported as absorbance increase at 490 nm per minute per mg of membrane). The results of these determinations are shown in Table 4. It is apparent that the retention of enzyme activity is not dependent upon a carrier protein such as BSA since significant activity is recovered without it in the formulation. However, the highest enzyme activity was recovered at an intermediate level of BSA, indicating that some carrier is useful.

TABLE 4

Retained Horseradish Peroxidase Activity in membranes

| BSA (Initial %) | Protein (mg/g) | HRP Activity (A490/min/mg of membrane) |
| --- | --- | --- |
| 0.0 | ND* | 0.007 (0.001) |
| 0.25 | 0.42 (0.11) | 0.156 (0.088) |
| 1.0 | 1.34 (0.05) | 0.111 (0.015) |
| 2.5 | 2.65 (0.11) | 0.215 (0.080) |
| 5.0 | 3.58 (0.78) | 0.079 (0.023) |

*ND = None detected

EXAMPLE 15

This example shows that alkaline phosphatase can be bound at surfaces of these biomosaic polymer membranes. Membranes were prepared as in Example 2 where the aqueous solution contained 0.025% alkaline phosphatase ("Type VII-T", Sigma Chemical Co.) and 1.0 mM magnesium chloride and zinc chloride in 1% BSA in water and the surface active agent was "Aerosol OT", "Triton X-100", "Pluronic L81", "Pluradot HA410", or "Igepal CO850". The retained enzyme activity was assayed with p-nitrophenylphosphate by the Sigma method (Sigma Chemical Co., 1988 catalog page 1139). The results are shown in Table 5.

TABLE 5

Retained Alkaline Phosphatase Activity in Membranes

| Surface Active Agent | Phosphatase Activity (A410/hour/mg of membrane) |
| --- | --- |
| Aerosol OT | 0.0038 |
| Triton X-100 | 0.0742 |
| Pluronic L81 | 0.0139 |
| Pluradot HA410 | 0.0073 |
| Igepal CO850 | 0.0391 |

The 20-fold range of recovered enzyme activity found in these membranes may be due to a combination of the influence of the surface active agent interaction of the protein and monomer emulsion phases and inhibition of the enzyme by the surface active agent preparation.

EXAMPLE 16

This example shows that proteins other than BSA can be substituted as a carrier protein. Membranes were prepared with aqueous solutions of pig skin gelatin, 1% in PBS (Sigma Chemical Co.); casein, saturated in PBS solution (Sigma Chemical Co.); or human hemoglobin, saturated in PBS solution (Worthington Biochemical Co. of Malvern, Pa.) and 0.025% horseradish peroxidase as in Example 12. Enzyme activities, determined as in Example 14, were 0.010, 0.156, and 0.050 A490-/min/mg of membrane, respectively. This indicates that other proteins can be used as a carrier for biologically active molecules.

EXAMPLE 17

This example demonstrates the usefulness of antigen bound at surfaces of biomosaic polymer membranes. A membrane was prepared as in Example 2 from an aqueous solution containing 0.05% perennial ryegrass (PRG) pollen extract (3M Diagnostic Systems of Santa Clara, Calif.) in 1% BSA in water. The surface active agent used in this membrane was "Aerosol OT". Paper punch samples of this membrane were placed into the wells of a microtiter filtration plate with a nitrocellulose membrane bottom (Millipore Corporation of Bedford, Mass.) which had previously been wetted with 100 μl of 20% methanol in PBS, followed by 200 μl of PBS, and incubation with three 100 μl portions of 1% BSA in PBS, each for five minutes. (Solutions added to the membrane wells were drawn through by vacuum.) The biomosaic polymer membranes were treated with 100 μl of 1% HSA in PBS for 5 minutes, and then the solutions were drawn through the membrane by applying a vacuum.

FloroFAST TM kit "D" calibrator (available from 3M Diagnostic Systems) was diluted with 1% human serum albumin (HSA) in PBS such that final concentrations of IgE antibody to PRG were 20, 10, and 5 IUs per ml. Aliquots, 100 μl each, of these solutions were incubated in the wells for 30 minutes at ambient temperature followed by thorough washing with Specific IgE FAST TM Wash Buffer (3M Diagnostic Systems). The membranes were then incubated for an additional 30 minutes with 100 μl of Specific Anti-IgE-Enzyme Conjugate (3M Diagnostic Systems) in Specific IgE FAST TM Conjugate Buffer followed by a repeat of the washing procedure. The membranes were then assayed for bound enzyme conjugate with Specific IgE FAST TM Substrate solution (3M Diagnostic Systems). After 30 minutes of incubation one set of the solutions was transferred to clean black polystyrene wells in a microtiter plate and its fluorescence read using the FluoroFAST TM microtiter well fluorometer (3M Diagnostic Systems).

Figure 2:
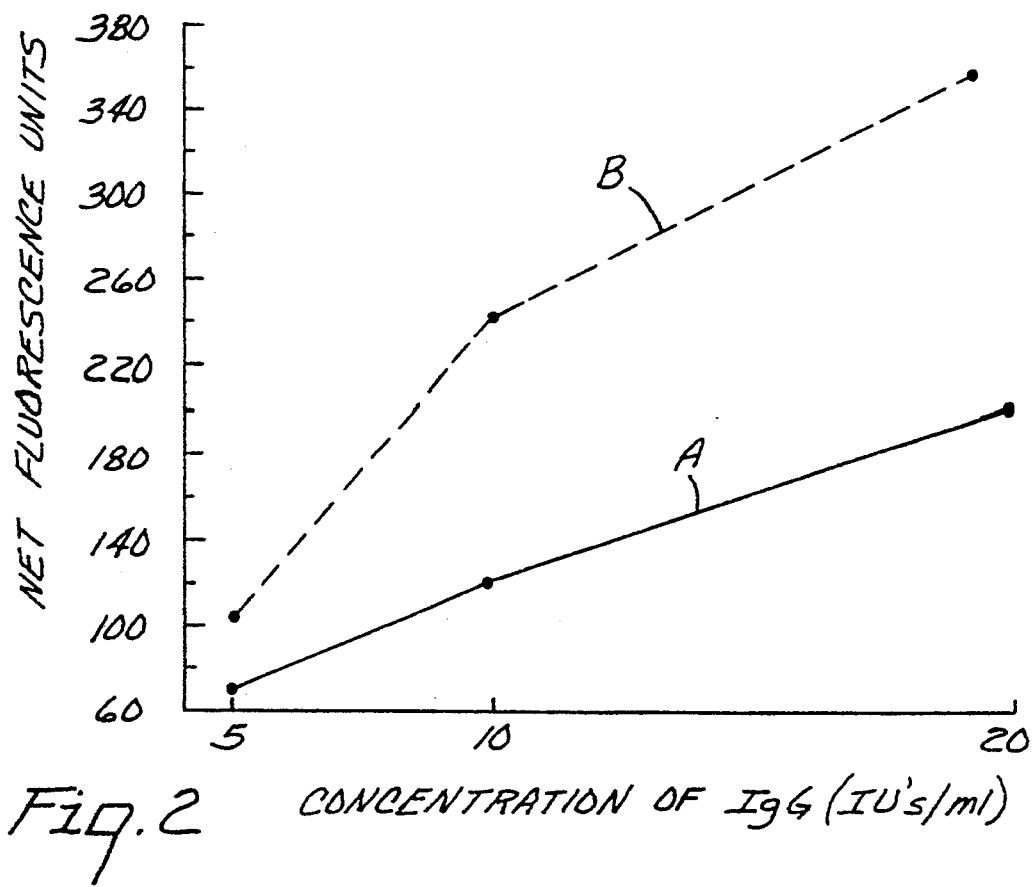
FIG. 2 is a graph showing the results of Example 17 described below.

The procedure was repeated with another set after 60 minutes of incubation. FIG. 2 shows that the fluorescence response increases nearly linearly with the concentration of PRG-specific IgE present in the sample solutions after 30 minute (line A) and 60 minute (line B) incubations. This response indicates that the antigenic activity of the extract was retained and that such membranes can be used to determine the amount of an antibody present in serum samples.

EXAMPLE 18

Figure 3:
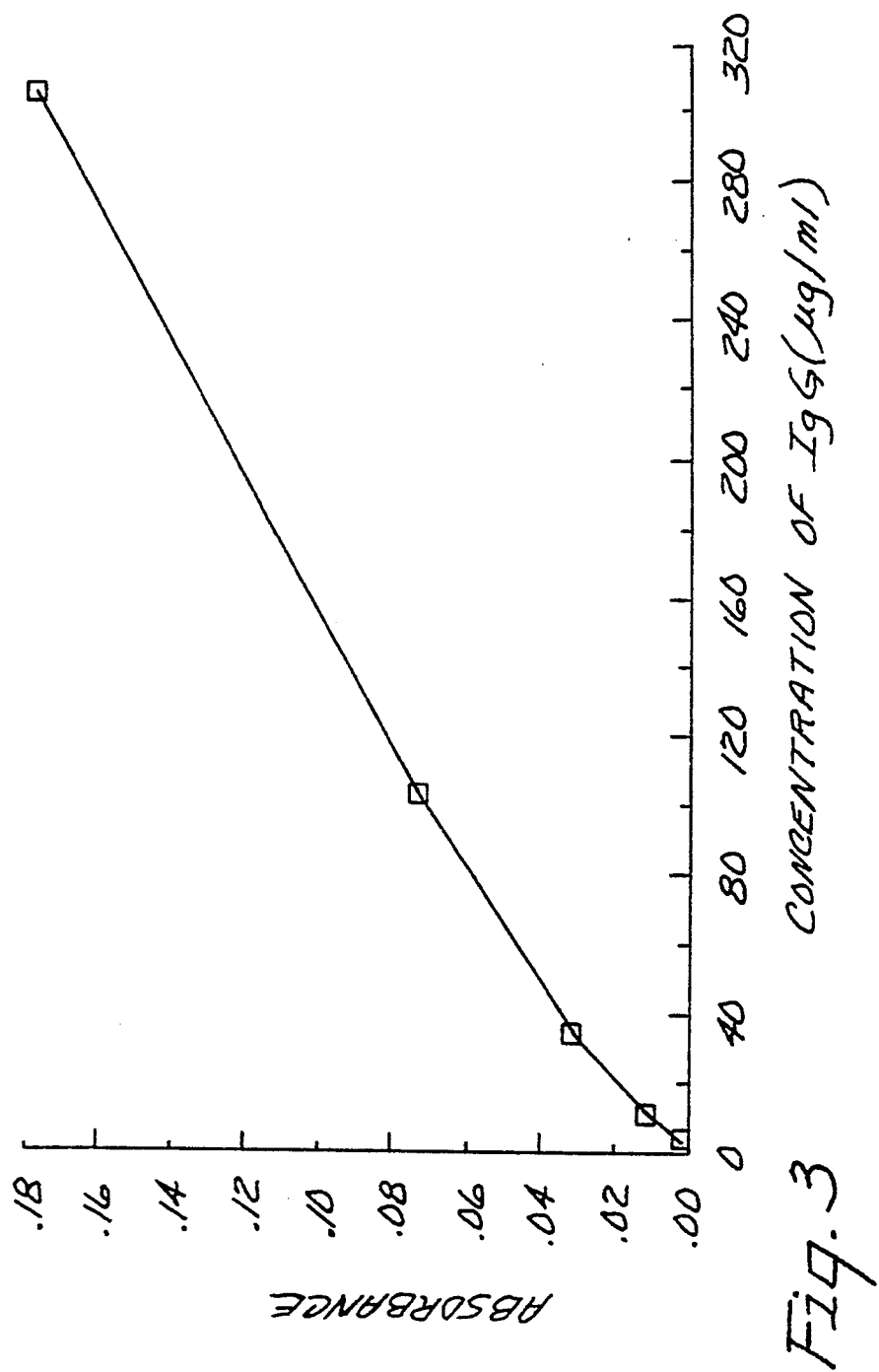
FIG. 3 is a graph showing the results of Example 18 described below.

This example demonstrates the usefulness of antibody biomosaic polymer membranes. A membrane was prepared as in Example 2 from an aqueous solution containing 0.05% sheep anti-human IgG antibody (available from CooperBiomedical of Malvern, Pa.) and 1% BSA in water. The surface active agent used in this preparation was "Aerosol OT". Paper punch samples of this membrane were placed in the wells of a microtiter filtration plate pretreated as in Example 17. The membranes were then wetted with 100 μl of 1% BSA in PBS for 5 minutes and the solution was drawn through the membrane under vacuum. A solution of 300 μg/ml of human IgG and 5 μg/ml of human IgG conjugated to HRP (both from CooperBiomedical) in 1% BSA was diluted to final concentrations of 102, 34, 11, and 4 μg/ml with 1% BSA. Aliquots, 100 μl each, of these solutions were added to the membranes and allowed to incubate for 5 minutes before being drawn through. Each well and membrane was then thoroughly washed with 0.1% solution of "Tween 20" in PBS. ("Tween 20" surface active agent is available from Sigma Chemical Co.). The bound HRP was assayed for 10–15 minutes as in Example 14. The absorbances of the resulting solutions were read by transferring them to a clear flatbottom polystrene microtiter plate and measuring their 490 nm absorbance on a Dynatech microplate reader (Dynatech Corporation of Chantlily, Va.). FIG. 3 shows that there is a nearly linear correlation of absorbance to IgG concentration shown in line A. This example shows that the biomosaic polymer membrane can be used to determine the amount of antigen in a biological sample.

EXAMPLE 19

This example shows that the protein bound during polymerization is overwhelmingly congregated at the surfaces of the biomosaic polymer so formed. Two membranes were prepared by the method of Example 2 with the emulsion components and weight fractions being that for membrane 5 of Table 1, except that one emulsion's hydrophilic liquid contained no human serum albumin and the other emulsion's hydrophilic liquid contained 5.0% human serum albumin (HSA). The membranes prepared were analyzed by x-ray photoelectron spectroscopy (XPS) using a Hewlett-Packard Model "5950B" ESCA Spectrometer machine (available from Hewlett-Packard, of Palo Alto, Calif.) to determine the elemental content of the surface of the membrane to a depth of from at least 40 Angstroms to as much as 100 Angstroms.

The spectrometer was set according to the instructions contained in its operations manual except as follows: a concentric hemispherical analyzer and a flood gun set at 2–4 milliamperes and 4–5 electron volts were used; an 800 watt monochromatic x-ray beam using Al-K-alpha x-rays was used; and as a reference, the carbon 1s signal at 285 electron volts was used.

Since the only source of elemental nitrogen in these membranes is the protein, the level of nitrogen found by XPS indicated the amount of protein bound at surfaces of the biomosaic polymer membranes. Table 6 shows the results obtained.

TABLE 6

| Membrane | XPS Elemental Analysis (%) | | |
|---|---|---|---|
| HSA (%) | Carbon | Oxygen | Nitrogen |
| 0.0 | 72 | 28 | 0.0 |
| 5.0 | 71 | 27 | 2.3 |

The magnitude of the elemental nitrogen found by XPS analysis of the surface indicated that an unexpectedly large amount of protein was bound there.

Nitrogen comprises only about 14.3% of the non-hydrogen atoms of protein. An emulsion having a protein content of 1.6% (5% HSA times 0.32 P/MS) had only about 0.2% nitrogen. If all of the emulsion's protein were combined with the hydrophobic polymerizable monomer during polymerization, and if the protein were evenly distributed throughout the mass of the polymer, the XPS surface elemental analysis would also show 0.2% nitrogen. Ten times that amount was unexpectedly measured at the surface of the biomosaic polymer membrane. Thus, the protein was congregated overwhelmingly at the surface of the biomosaic polymer.

If the depth of penetration of the x-ray analysis were limited to the minimum of about 40 Angstroms, about the longest dimension of HSA, the percentage of the surface area of the polymer comprising biologically active material would be calculated to be at least about 16%, or the ratio of measured elemental nitrogen found at the surface to the total elemental nitrogen theoretically possible at the surface: 2.3/14.3.

As seen in Example 11, about 34% of the albumin was found to be bound. If the efficiency of binding in this Example were the same as that found in Example 11, and if the efficiency of binding could then be increased to as much as the 90% believed possible according to the present invention, then the surface area of the polymer comprising the biologically active material could be at least as much as about 42% of the total surface area.

It is known that the depth of penetration of the x-ray analysis depends on the material's properties and the power of the x-ray beam. If the depth of penetration were greater than 40 Angstroms (as is known to frequently occur at least twice as far), e.g., to a depth of 80 Angstroms, (well within the state of the art) then the theoretical percentage of nitrogen would at least be halved, and percentage surface area of biologically active material previously calculated in this Example would at least double from 16% to 32% and from 42% to 84%.

While embodiments of the invention and examples have been disclosed, the scope of the invention is not limited to them but found in the claims below.

What is claimed is:

1. A porous, polymeric membrane, comprising:
   a polymer formed from at least one monomer consisting essentially of hydrophobic polymerizable addition-polymerizable unsaturated organic compound having at least one double bond between two carbon atoms and having a solubility in water of less than 1 part in 100 parts (weight/weight) of water;
   said polymer having porous surfaces, with pores of from about 0.01 micrometers to about 10 micrometers, capable of diffusing aqueous solutions without difficulty through the porous, polymeric membrane, and said polymer having at least a minimally useful amount of at least one biochemical compound, irreversibly bound at and becoming a part of said porous surfaces of said polymer during formation of said polymer and biologically active, said surfaces, comprising outer surfaces of said membrane and surfaces of said pores of said membrane, having an elemental content including elements of said polymer and elements of said biochemical compound wherein said biochemical compound is congregated at said surfaces for reaction with compounds in the aqueous solutions, wherein the porous, polymeric membrane is prepared from a polymerization of a water-in-oil or bicontinuous emulsion comprising said hydrophobic polymerizable monomer, said biochemical compound and at least one surface active agent;

wherein said polymerization occurs at no less than about ambient temperature;

wherein said hydrophobic polymerizable monomer comprises from about 1 to about 97 weight percent of said emulsion;

wherein said biochemical compound is in a hydrophilic liquid capable of forming an emulsion or microemulsion with the hydrophobic polymerizable monomer, the amount of said biochemical compound in said hydrophilic liquid is less than saturation amount, and said hydrophilic liquid comprises of from about 1 to about 97 percent of said emulsion; and wherein said surface active agent is in said emulsion in an amount of from about 2 weight percent to about 97 percent of said emulsion.

2. The porous, polymeric membrane according to claim 1, wherein said hydrophobic polymerizable monomer comprises a monofunctional acrylate, a multifunctional acrylate, or combinations thereof;

wherein said surface active agent is in said emulsion in an amount of from about 10 weight percent to about 60 percent of said emulsion.

3. The porous, polymeric membrane according to claim 2, wherein said biochemical compound comprises at least one amino acid, carbohydrate, lipid, nucleic acid, protein, antibody, antigenic substance, enzyme, co-factor, inhibitor, lectin, hormone, receptor, coagulation factor, growth enhancer, histone, vitamin, drug, cell surface marker, herbicide, pesticide, or combinations thereof.

4. The porous, polymeric membrane according to claim 3, wherein said hydrophobic polymerizable monomer comprises isooctyl acrylate, isobornyl acrylate, 2-ethylhexyl acrylate, ethylenediglycol acrylate, ethyltriglycol methacrylate, 1,6-hexanediol diacrylate, tetraethyleneglycol diacrylate, tripropyleneglycol diacrylate, propoxylated glycol diacrylate, pentaerythritol triacrylate, trimethylolpropane triacrylate, pentaerythritol tetraacrylate, di-trimethylolpropane tetraacrylate or combinations thereof in said emulsion in an amount of from about 25 to about 80 weight percent of said emulsion.

5. The porous, polymeric membrane according to claim 3, wherein from about 5 percent to about 75 percent of said biochemical compound in said emulsion during said polymerization of said hydrophobic polymerizable monomer is irreversibly bound to said surfaces of said polymer after said polymerization.

6. The porous, polymeric membrane according to claim 3, wherein as little of said biochemical compound as is minimally useful to as much of said biochemical compound as about 70 $\mu g/cm^2$ of said membrane is bound at said surfaces of said porous membrane.

7. The porous, polymeric membrane according to claim 3, wherein as little of said biochemical compound as is minimally useful to as much of said biochemical compound as about 20 mg/g of said polymer is bound at said surfaces of said porous membrane.

8. The porous, polymeric membrane according to claim 3, wherein said biochemical compound comprises between as little of said surfaces as is minimally useful to as much of said surfaces as about 84 percent.

9. A method for the preparation of a polymeric membrane comprising:

mixing a water-in-oil or bicontinuous emulsion comprising at least a minimally useful amount of at least one biochemical compound, at least one hydrophilic liquid, at least one hydrophobic polymerizable monomer consisting essentially of at least one hydrophobic addition-polymerizable unsaturated organic compound having at least one double bond between two carbon atoms having a solubility in water of less than one part in 100 parts (weight/weight) of water, and at least one surface active agent; and polymerizing said emulsion at no lower than about ambient temperature to polymerize said hydrophobic polymerizable monomer to form a porous, polymeric membrane having said biochemical compound, irreversibly bound at and becoming part of the surfaces of said membrane during formation of said membrane and biologically active, said surfaces having an elemental content including elements of said polymer and elements of said biochemical compound wherein said biochemical compound is congregated at said surfaces in biologically active condition for biochemical, immunochemical, physiological or pharmaceutical reaction.

10. The method according to claim 9, wherein said biochemical compound comprises at Least one amino acid, carbohydrate, lipid, nucleic acid, protein, antibody, antigenic substance, enzyme, co-factor, inhibitor, lectin, hormone, receptor, coagulation factor, growth enhancer, histone, vitamin, drug, cell surface marker, herbicide, pesticide, or combinations thereof.

11. The method according to claim 9, where said hydrophobic polymerizable monomer comprises from about 1 to about 97 weight percent of said emulsion.

12. The method according to claim 11, wherein said hydrophobic polymerizable monomer comprises a monofunctional acrylate, multifunctional acrylate, or combinations thereof in said emulsion in an amount of from about 25 to about 80 weight percent of said emulsion.

13. The method according to claim 11, wherein said hydrophobic polymerizable monomer comprises isooctyl acrylate, isobornyl acrylate, 2-ethylhexyl acrylate, ethylenediglycol acrylate, ethyltriglycol methacrylate, 1,6-hexanediol diacrylate, tetraethyleneglycol diacrylate, tripropyleneglycol diacrylate, propoxylated glycol diacrylate, pentaerythritol triacrylate, trimethylolpropane triacrylate, pentaerythritol tetraacrylate, di-trimethylolpropane tetraacrylate or combinations thereof.

14. The method according to claim 9, further comprising the step of placing said biochemical compound in said hydrophilic liquid prior to said mixing step, wherein the amount of said biochemical compound in said hydrophilic liquid is less than saturation amount, wherein said hydrophilic liquid comprises of from about 1 to about 97 weight percent of said emulsion, and wherein from about 1 percent to about 90 percent of said biochemical compound in said emulsion during said polymerization of said polymerizable monomer is irreversibly bound at said surfaces after said polymerization.

15. The method according to claim 14, wherein from about 5 percent to about 75 percent of said biochemical compound in said emulsion during said polymerization of said polymerizable monomer is bound at said surfaces after said polymerization.

16. The method according to claim 9, wherein said surface active agent comprises at least one ionic surface active agent, nonionic surface active agent, zwitterionic surface active agent, or combinations thereof in said emulsion in an amount of from about 2 weight percent to about 97 weight percent of said emulsion;

wherein said ionic surface active agent comprises a salt of a carboxylic acid having a carbon chain length of from about 8 to about 22 atoms, a sulfonic acid, a sulfuric acid ester, a phosphoric acid ester, a polyphosphoric acid ester, a quarternary ammonium salt, an oxide or salt of an amine compound having a carbon chain length of from about 8 to about 22 atoms, or a combination thereof;

wherein said nonionic surface active agent comprises a polyoxyethylenated-alkyl phenol, a polyoxyethylenated-straight chain alcohol, a polyoxyethylenated-polypropylene glycol, a carboxylic acid ester having a carbon chain length of from about 8 to 22 atoms, or a combination thereof; and wherein said zwitterionic surface active agent comprises a beta-N-alkylaminopropionic acid, a N-alkyl-beta-iminodipropionic acid, an imidazoline carboxylate, a N-alkylbetaine, a sulfobetaine, a sultaine or a combination thereof.

17. The method according to claim 9, further comprising, between the steps of said mixing and said polymerizing, the step of dispensing said emulsion into a desired form prior to said polymerizing.

18. The method according to claim 9, wherein said polymerizing comprises irradiating said emulsion with high energy radiation.

19. A method for the preparation of a biomosaic polymer according to claim 18, wherein said high-energy radiation is ultra-violet radiation.

20. The porous, polymeric membrane, according to claim 2, wherein the porous membrane comprises means for immunoassay.

21. The porous, polymeric membrane, according to claim 2, wherein the porous membrane comprises an enzyme reactor.

22. The porous, polymeric membrane, according to claim 2, wherein the porous membrane comprises a bioseparator.

* * * * *

UNITED STATES PATENT AND TRADEMARK OFFICE
CERTIFICATE OF CORRECTION

PATENT NO. : 5,405,618
DATED : April 11, 1995
INVENTOR(S) : Buttery et al.

It is certified that error appears in the above-indentified patent and that said Letters Patent is hereby corrected as shown below:

Column 20, line 41, "FloroFAST" should read --FluoroFAST--.

Column 23, line 38, "thereof;" should read --thereof; and--.

Column 24, line 43, "Least" should read --least--.

Column 26, lines 19-20, "for the preparation of a biomosaic polymer" should be deleted.

Signed and Sealed this

Twelfth Day of December, 1995

Attest:

BRUCE LEHMAN

*Attesting Officer*    *Commissioner of Patents and Trademarks*